United States Patent [19]

Price

[11] Patent Number: 5,353,787
[45] Date of Patent: Oct. 11, 1994

[54] ENDOTRACHEAL TUBE AND ORAL AIRWAY CONNECTOR

[76] Inventor: Evelyn C. Price, 5831 Rue Burgundy, San Antonio, Tex. 78240

[21] Appl. No.: 74,792

[22] Filed: Jun. 10, 1993

[51] Int. Cl.⁵ .................. A61M 16/00; A61M 5/32; A62B 9/06
[52] U.S. Cl. .................. 128/200.26; 128/207.14; 128/911; 128/912; 128/DIG. 26; 604/117; 604/174
[58] Field of Search ......... 128/200.26, 207.14–207.18, 128/911, 912, DIG. 26; 604/117, 100, 96, 174

[56] References Cited

U.S. PATENT DOCUMENTS

| | | | |
|---|---|---|---|
| 2,923,299 | 2/1960 | Blackwood | 128/207.17 |
| 3,039,469 | 6/1962 | Fountain | 128/200.26 |
| 3,459,175 | 8/1969 | Miller | 604/117 |
| 4,142,527 | 3/1979 | Garcia | 604/180 |
| 4,235,229 | 11/1980 | Ranford et al. | 128/207.17 |
| 4,269,184 | 5/1981 | Montgomery | 128/207.14 |
| 4,340,046 | 7/1982 | Cox | 128/200.26 |
| 4,471,776 | 9/1984 | Cox | 128/207.15 |
| 4,527,559 | 7/1985 | Roxburg et al. | 128/207.17 |
| 4,838,255 | 6/1989 | Lambert | 128/207.16 |
| 4,987,895 | 1/1991 | Heimlich | 128/207.14 |
| 5,083,561 | 1/1992 | Russo | 128/207.14 |
| 5,163,941 | 11/1992 | Garth et al. | 604/165 |
| 5,197,465 | 3/1993 | Montgomery | 128/200.26 |
| 5,253,643 | 10/1993 | Price | 128/DIG. 26 |

Primary Examiner—Kimberly L. Asher

[57] ABSTRACT

An endotracheal tube (38a) demountably attachable to and for use in combination with an oral airway (10) having a tabular flange (22) with C-shaped openings thereon, the endotracheal tube (38a) having an elongated hollow tubular body (56) with first open end (60) and a second open end (62), the body (56) having a portion containing alternating ribs (50) and bays (52) integral with the body of the endotracheal tube (38a). The bays (52) are dimensioned to fit snugly within the C-shaped opening of said oral airway (10) and the ribs (50) being dimensioned to prevent longitudinal displacement of the endotracheal tube (38a) with respect to the oral airway (10).

4 Claims, 2 Drawing Sheets

ENDOTRACHEAL TUBE AND ORAL AIRWAY CONNECTOR

FIELD OF THE INVENTION

An endotracheal tube used independently of or for use with and demountably attachable to an oral airway having a flange with C-shaped openings. More specifically, an endotracheal tube wherein a portion of the body has alternating pairs of annular bays with adjacent rib portions.

BACKGROUND

Hospitals use oral airways with acute care victims of accidents and the like for providing oral communication between a patient's throat and the patient's gaseous environment. More specifically, oral airways provide a means for depressing a patient's tongue to allow gaseous communication into a patient's lungs.

Endotracheal tubes are sometimes used in conjunction with oral airways to provide a means for introducing a gas, such as oxygen, directly into the trachea of the patient. For example, the invention disclosed in U.S. patent application No. 07/820,305, now U.S. Pat. No. 5,253,643, discloses a novel oral airway with a flange having a C-shaped opening to which to demountably attach an endotracheal tube. In the past, an endotracheal tube has been typically taped to an oral airway to prevent lateral and longitudinal displacement between the oral airway and the endotracheal tube, that is, to stabilize the endotracheal tube with respect to the oral airway. The oral airway is then typically fixed to the patient by means for a cord or tape wrapped about the patient's head.

It is important to stabilize the endotracheal tube with respect to the oral airway as the depth to which the endotracheal tube is inserted into the patient's trachea is critical. To ensure proper intubation, the doctor must not insert the endotracheal tube either too shallow or too far into the patient's trachea. Heretofore, a need has existed for an endotracheal tube which will not slide longitudinally along an oral airway when attached to the oral airway.

Thus, it is one of the objects of the present invention to provide an endotracheal tube attachable to an oral airway, for example, with an oral airway having C-shaped openings while providing a means for preventing longitudinal displacement of the endotracheal tube with respect to the oral airway.

SUMMARY OF THE INVENTION

This and other objects are provided for in an endotracheal tube having a means engageable with a C-shaped opening of an oral airway, said means for preventing longitudinal displacement of the endotracheal tube with respect to the oral airway.

It is a further object of the present invention to provide for a means of preventing longitudinal displacement of an endotracheal tube with respect to an oral airway, said preventing means comprising a multiplicity of sets of annular alternating ribs and bays integral with the body of said endotracheal tube, the bays being dimensioned to fit snugly within a C-shaped opening of the flange of said oral airway.

It is a further object of the present invention to provide for an endotracheal tube having a means to prevent longitudinal displacement with an oral airway to which the endotracheal tube is demountably attached, the preventing means also providing numerals for determining the depth which the endotracheal tube is inserted into the patient's trachea.

DETAILED DESCRIPTION OF THE PREFERRED EMBODIMENT

For the sake of clarity, this application utilizes the same nomenclature and numerical designations for the oral airway disclosed and claimed in U.S. patent application No. 07/820,305 but is not intended to be limited to use with the oral airway disclosed therein.

Figure 1:
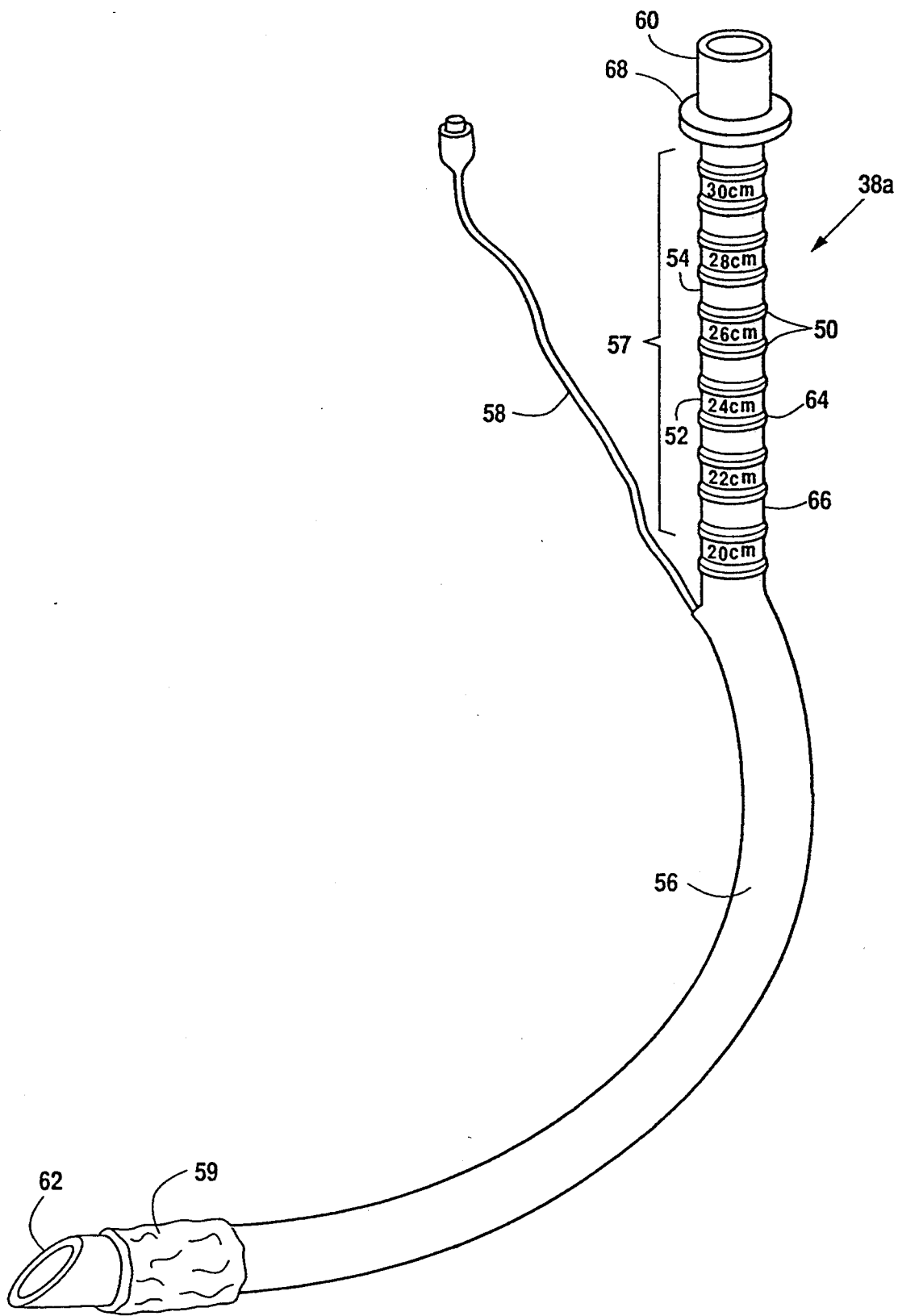
FIG. 1 is a side elevational view of the endotracheal tube of Applicant's present invention.
Figure 2A:
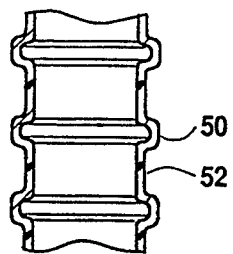
FIGS. 2A and 2B are alternate preferred embodiments illustrating cross-sectional views of the alternating bays and ribs of Applicant's present invention taken perpendicular to the plane of the annular rings representing ribs and bays.
Figure 2B:
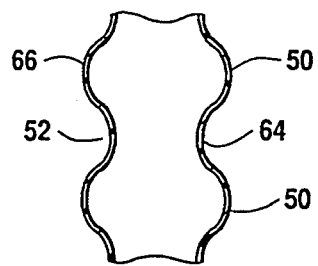
Figure 2:
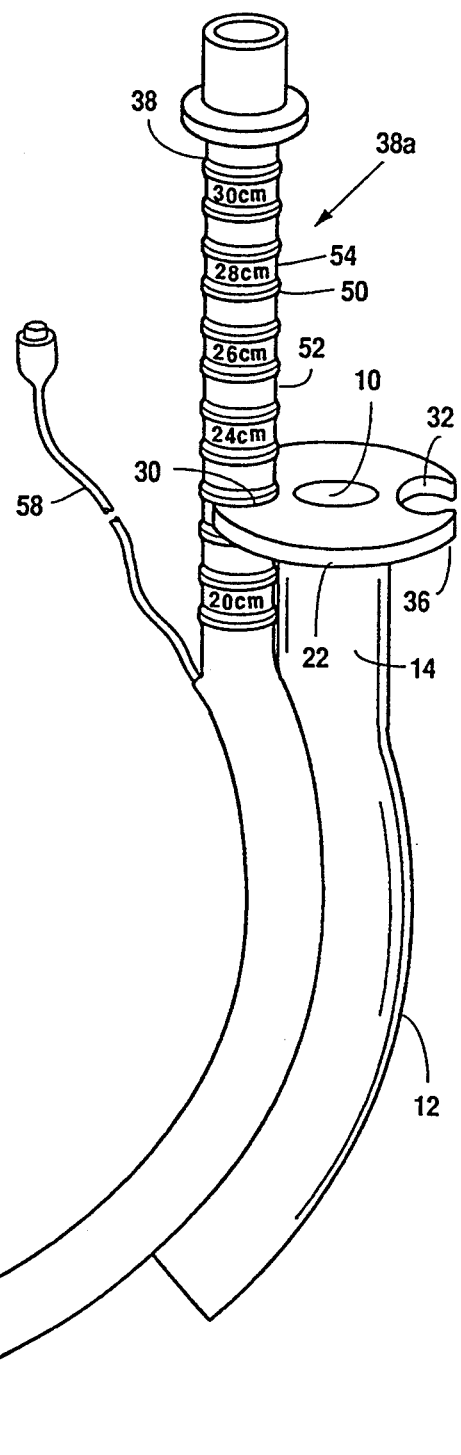
FIG. 2 is a side view in perspective of the endotracheal tube of Applicant's present invention as used in conjunction with an oral airway having a C-shaped opening for demountably attaching the endotracheal tube thereto.

FIGS. 1 and 2 disclose the novel endotracheal tube (38a) of Applicant's present invention. More specifically, FIGS. 1 and 2 illustrate endotracheal tube (38a) having a body (56) with a near end (60) and a removed end (62). Line (58) joins body (56) and is typically found in endotracheal tubes to provide a means of introducing gas to inflate balloon (59).

The novelty of Applicant's endotracheal tube (38a) lies in providing a series of ribs or projections (50) separated by grooves or bays (52). Alternating sets of ribs (50) and bays (52) are annular with bays (52) or ribs (50) having indicia (54) thereon to indicate the depth to which endotracheal tube (38a) is inserted into the patient.

Walls (64) of ribs or projections (50) define a smooth curve. The importance of the smooth or rounded curve to the cross-section of ribs (50) lies in allowing smooth contact with a patient's mouth, lips, tongue, throat, trachea or other delicate membrane. That is, if ribs (50) had sharp edges or were angular in nature, it is more likely that the patient's fragile membrane may be irritated by contact between the ribs and the patient. Walls (66) of grooves or bays (52) are simply annular rings which typically join walls (64) of ribs (50) in a generally perpendicular relation, but may alternately be concave.

Thus, it is seen how body (56) has a ribbed portion (57). Moreover, it is seen in FIG. 2 how endotracheal tube (38a) is engageable with attachment means (30) and (32) of flange plate (22) of oral airway (10). Specifically, it is noted that the outer diameter of projections or ribs (50) is greater than the diameter of C-shaped attachment means (30) and (32). The outer diameter of grooves or bays (52) is sufficient to snugly fit within C-shaped openings defining attachment means (30) and (32). Thus, in the manner illustrated in FIG. 2, endotracheal tube (38a) may be placed adjacent to lips (36) of attachment means (30) and (32) at bays (52) and urged laterally towards the longitudinal axis of oral airway (10). Endotracheal tube (38a) will "snap fit" into oral airway (10) with indicia (54) defining the distance endotracheal tube (38a) is inserted into the trachea of the patient and with ribs (50) preventing longitudinal displacement of endotracheal tube (38a) with respect to oral airway (10). Endotracheal tube (38a) will be maintained in a stable position by interference with the walls of flange (22). It is further apparent from FIG. 2 that each bay (52) or rib (50) will define a different depth into which endotracheal tube (38a) is inserted into the patient's trachea. That is, flange (22) is fixedly located at the patient's lips and the health care professional can determine the depth to which the endotracheal tube (38a) should be inserted and place the endotracheal tube with bay (52) corresponding to such depth adjacent lips (36). At this point, oral airway (10) and endotracheal tube (38a) should be joined by a snap fit. Ribs (50) adjacent bays (52) will prevent substantial longitudinal movement of endotracheal tube (38a) with respect to oral airway (10). Moreover, the use of a multiplicity of bays, each with adjacent ribs (50) provides the health care professional with a multiplicity of choices to which endotracheal tube (38a) may be inserted into the patient, with respect to the chorina.

It is to be understood that the specifications and claims, while disclosing an endotracheal tube suitable for use with or without the device claimed in the '305 patent application, is suitable for use with any flanged oral airway having attachment means in which alternating bays and ribs will prevent substantial longitudinal displacement.

Indicia on ribbed portion (57) are typically in the range of 10 cm. to 30 cm. The difference between the outside diameter of the ribs (50) and the bays (52) is typically in the range of 1 min. to 4 min.

FIGS. 2A and 2B represent cross-sectional views taken perpendicular to the plane of the alternating ribs and bays. FIG. 2A illustrates and alternate preferred embodiment in which the cross-section of ribs (50) is substantially smooth curve and wherein the bays are defined by the flat walls connecting the walls of adjacent ribs. FIG. 2B, on the other hand, illustrates bays (52) having a concave outline which flows smoothly into the curve of ribs (50). In both cases, ribs (50) represent smooth, curved projections which will not cause abrasion or interference with the delicate membranes of the patient's mouth.

The endotracheal tube (38a) can be used independently of the oral airway as typical endotracheal tubes are presently used.

Terms such as "left", "right", "up", "down", "bottom", "top", "front", "back", "in", "out" and the like are applicable to the embodiment shown and described in conjunction with the drawings. These terms are merely for the purposes of description and do not necessarily apply to the position or manner in which the invention may be constructed or used.

Although the invention has been described in connection with the preferred embodiment, it is not intended to limit the invention to a particular form set forth, but on the contrary, it is intended to cover such alternatives, modifications, and equivalents as may be included within the spirit and the scope of the invention as defined by the appended claims.

I claim:

1. A system for providing fluid communication for the passage of a gas from a patient's mouth to the throat and into the treachea, the system comprising:

an oral airway consisting essentially of an elongated tubular body having a first open end defining a first orifice and a second open end defining a second orifice and an annular plate, integral with the first open end of said tubular body, the plate having a top surface and a bottom surface, the top surface and the bottom surface joined by a perimeter, the perimeter having walls defining means for demountably attaching an endotracheal tube thereto, wherein the attaching means of the plate has a first pair of resilient lips and a second pair of resilient lips, each pair formed into a "C" shape, each one lip of each pair being oppositely disposed from the other lip of the pair and having a distance between them that is less than the outside diameter of an endotracheal tube;

said endotracheal tube consisting essentially of an elongated, hollow, tubular body having a first open end and a second open end, the body of said endotracheal tube having means engageable with said "C"-shaped openings of said oral airway for preventing longitudinal and lateral displacement of said endotracheal tube with respect to said oral airway when said endotracheal tube is engaged with the "C"-shaped opening of said oral airway; and wherein said preventing means of said endotracheal tube includes a multiplicity of pairs of annular alternating ribs and bays integral with the body of said endotracheal tube, the bays being dimensioned to fit snugly within the "C"-shaped opening of the plate, the ribs dimensioned to exceed the diameter of the "C"-shaped opening of the plate of said oral airway.

2. The system as described in claim 1, wherein the bays of said preventing means have indicia thereon.

3. The system as described in claim 1, wherein the bays of said preventing means have straight walls connecting adjacent ribs, the ribs having vertical walls perpendicular to the straight walls of the bays.

4. The system as described in claim 1, wherein said bays have a concave cross-section.

* * * * *